US008470259B2

(12) United States Patent
Gupta

(10) Patent No.: US 8,470,259 B2
(45) Date of Patent: Jun. 25, 2013

(54) METHOD AND DEVICE FOR PARTICLE REMOVAL AND DROPLET PREPARATION FOR QUALITATIVE AND QUANTITATIVE BIOANALYSIS

(75) Inventor: Nalini Kant Gupta, Haryana (IN)

(73) Assignee: Advanced Microdevices Pvt Ltd, Haryana (IN)

( * ) Notice: Subject to any disclaimer, the term of this patent is extended or adjusted under 35 U.S.C. 154(b) by 304 days.

(21) Appl. No.: 12/921,265

(22) PCT Filed: Feb. 2, 2009

(86) PCT No.: PCT/IN2009/000133
§ 371 (c)(1),
(2), (4) Date: Sep. 7, 2010

(87) PCT Pub. No.: WO2009/109997
PCT Pub. Date: Sep. 11, 2009

(65) Prior Publication Data
US 2011/0041591 A1    Feb. 24, 2011

(30) Foreign Application Priority Data
Mar. 7, 2008  (IN) .............................. 563/DEL/2008

(51) Int. Cl.
*C02F 1/00*    (2006.01)
(52) U.S. Cl.
USPC ........... 422/402; 422/68.1; 422/534; 422/527

(58) Field of Classification Search
None
See application file for complete search history.

(56) References Cited

U.S. PATENT DOCUMENTS

| 4,587,102 | A  | * | 5/1986  | Nagatomo et al. ............ 422/421 |
| 4,753,776 | A  |   | 6/1988  | Hillman et al. |
| 4,816,224 | A  |   | 3/1989  | Vogel et al. |
| 4,849,347 | A  |   | 7/1989  | Familletti et al. |
| 5,055,195 | A  |   | 10/1991 | Trasch et al. |
| 5,101,720 | A  | * | 4/1992  | Bianchi ......................... 100/99 |
| 6,555,061 | B1 | * | 4/2003  | Leong et al. .................. 422/412 |
| 2004/0222168 | A1 | * | 11/2004 | Frey et al. ..................... 210/767 |

FOREIGN PATENT DOCUMENTS
EP    1421993 A    5/2004

* cited by examiner

*Primary Examiner* — Yelena G Gakh
*Assistant Examiner* — Christopher A Hixson
(74) *Attorney, Agent, or Firm* — Dergosits & Noah LLP

(57) ABSTRACT

This disclosure provides a method and device for particle removal and droplet preparation for qualitative and quantitative bioanalysis. In one embodiment, the disclosed device includes a lateral flow filter through which the sample is filtered such that the filtrate fluid is collected in the distal end of the filter matrix. The filtered fluid is made to eject from the matrix to form a droplet by pressing/squeezing the distal end of the filter only, with the help of a suitably shaped plunger means.

12 Claims, 6 Drawing Sheets

METHOD AND DEVICE FOR PARTICLE REMOVAL AND DROPLET PREPARATION FOR QUALITATIVE AND QUANTITATIVE BIOANALYSIS

TECHNICAL FIELD

This disclosure relates generally to devices and methods for removing particles from fluids and making droplets of filtered fluid in free form as pure liquid without any filter matrix for qualitative and quantitative bioanalysis, and more particularly to, a device for separating RBCs from blood and preparing a droplet of blood plasma for Point of Care applications.

BACKGROUND ART

Analysis of analytes in various biological fluids is of great interest for the diagnosis of diseases and disorders. Generally, the presence of particulates and cellular matter in the fluids interfere with the assay procedures. For example, when analyzing for analytes in blood, the removal of Red Blood Cells (RBC) is often necessary to get meaningful results.

Conventional methods such as centrifugation, sedimentation, etc can be readily used to separate RBCs. However, the conventional methods suffer from the disadvantage that they require separate equipment and technician time for separation of RBC. They also require availability of larger volume of patient sample, as plasma is difficult to separate cleanly from very small quantity of samples of blood.

The above-mentioned factors make the conventional methods unacceptable for 'point of care' (POC) or 'near patient' applications, which involve rapid test results with user-friendly equipments used by minimally trained staff. Increasingly, the need is felt for 'Point of Care' devices, which can help deliver quantitative results of similar quality as obtained from laboratory analyzers.

Several patents describe materials and devices to accomplish RBC and particulate removal from biological fluids. U.S. Pat. Nos. 4,816,224, 5,186,843, 5,240,862 teach variety of materials and devices which can be used to separate RBC from whole blood. U.S. Pat. Nos. 4,980,297, 5,135,719, 5,064,541, 5,139,685, EP1315553, EP1096254B1, U.S. Pat. Nos. 6,296,126B1, 6,197,598B1 and 6,391,265B1, 7,279, 136 describe devices and methods for separating plasma from whole blood and integrating these devices with various detection methods and 'Point of Care' instruments for detection and quantitation of analytes.

Many of the above inventions suffer from the fact that the fluid path for sample fluid is relatively short in the transverse direction resulting in low efficiencies of retention and leakage of particulate matter. This problem is overcome in some prior art inventions by adopting lateral flow of the sample which results in chromatographic separation of particulate matter and plasma is separated. Further retention is sought to be improved by region specific compression.

U.S. Pat. No. 6,391,265 titled "Devices incorporating filters for filtering fluid samples" discloses devices and use thereof, the device comprising a filter and a means for region specific compression of the filter. Alternatively, a single step assay device whereby fluid movement through the device occurs substantially solely due to action of capillary force, the device comprising a filter, a region containing the filter, a fluid access port to the region containing the filter, a means for retarding movement of particles through a peripheral filter surface, a fluid egress port from the region containing the filter, a lateral fluid flow path through the filter connecting the fluid access port to the fluid egress port, whereby sample fluid substantially devoid of particulate matter is released from the filter through the egress port; and, an exit region fluidly connected to the egress port.

The above mentioned prior art devices which do utilize long path length by lateral flow of sample and selective compression of filter and sealing of extraneous capillaries which can cause leakage of particulate matter tend to use large amounts of blood to achieve very small amounts of plasma. The plasma is obtained in a reaction zone capillary of less than 25 micron channel height.

U.S. Pat. No. 5,064,541 shows the uses of agglutinating agents in the sintered porous material to retain RBC and remove the separated plasma by wicking it with a matrix. By making the matrix of reproducible fluid uptake a measured amount of plasma is available in the matrix.

Due to short path lengths, not only do these devices suffer from poor retention but the free or pure plasma is not available as there is no provision to remove the pure plasma from the matrix.

US Patent Application 2004/0035792A1 describe a method where whole blood is placed into a feed chamber which is isolated by means of a membrane from a closed cavity having small height such that its capillary forces are higher than that of the separation membrane. The whole blood is filtered by means of forces of suction, pressure, capillary forces and or hydrostatic pressure to the capillary with small height where filtered plasma in pure liquid form is available. A method of removal of pure plasma by application of pressure on the sample (blood) feed or by applying suction on the plasma collected in the small height capillary is also described.

It is well known that when whole blood is filtered by applying pressure, it has to be done extremely slowly as the interstecial space of filter are filled with the RBC and with increasing pressure they will rupture contaminating the plasma. This makes application of pressure to recover plasma impractical in above invention. Removal of plasma by vacuum and making it available to reaction zones with large capillary heights or cuvettes or tubes requires complicated mechanical device and driving systems making the device costly and more difficult to use.

U.S. Pat. No. 6,296,126B/describes micromachined device with wedge shaped cutouts in contact with separated plasma in the matrix. The wedge shaped cutouts facilitate the removal of liquid from the matrix.

These devices suffer from very low recoveries of pure liquid and high cost of manufacture.

U.S. Pat. No. 7,404,931 discloses a device for plasma separation which has a separation element designed to comprise a separation zone and a transport zone. The separation zone separates the plasma from whole blood and transports it to the transport zone. A plunger system is incorporated in the device to detach the transport zone from the separation zone to collect the separated plasma.

The device of the '931 patent is restricted in its application in the sense that it completely detaches the transport zone from the separation zone thus negating any chance of recovery of residual plasma from the separation zone. In case of limited availability of blood sample, particularly with neonatal blood, such recovery of residual plasma become a critical parameter of checking the efficiency of such devices.

For 'Point of Care' (POC) tests with whole blood, it is very desirable to work with minimum amount of blood and obtain a quantitative amount of pure, undiluted plasma for analysis. With the advent of microfluidic devices it is even more desirable to have a means to deliver required amount of plasma to capillaries comprising reaction and reading zones of the POC devices.

The problem with above known methods to deliver plasma to capillaries is even more acute when the capillary itself is the reaction and reading zone. To achieve high sensitivities it is often necessary to keep capillary height of reading zones to greater than 25 microns and more close to 100 microns or greater. In such capillaries the filtered fluid accumulated at the distal end of the filter remains entrapped in the matrix and does not migrate into large height capillaries or reaction zones or reservoir from where it may be transferred to reaction cuvettes as the capillary forces are not strong enough to draw the filtered fluid out of the matrix.

Thus there exists a need for a simple, cost effective device which allows rapid and efficient removal of particulate matter from fluids to be analysed and delivers the filtered fluid in free form or droplet form without entrapment in the matrix or small height capillary so that the fluid can flow into open tanks or reaction zones or other zones with capillary forces lower than that of the matrix or capillary holding the filtered fluid. Moreover, such a device should be able to effectively collect a substantial volume of residual plasma that has failed to be transported to a transport zone in a first filter pass.

Such a device may be used separately or it can be easily integrated for qualitative and quantitative analysis with many different types of Point of Care and other instruments.

OBJECTS OF THE DISCLOSURE

An object of the invention is to provide a device and method for particulate removal from the sample and droplet preparation of filtered fluid such that the filtered fluid is able to flow into open tanks or zones with weaker capillary forces than the matrix or capillary holding the filtered fluid without the need for a separate equipment.

An object of the present disclosure is to provide a particle removal and droplet preparation device for separating RBC from blood and to rapidly achieve high yields of plasma with minimum use of whole blood.

Another object of the present disclosure is to provide a particle removal and droplet preparation device wherein the device may be used for filtering particulate matter from not only blood but also from fluids such as, for example, fecaes, plant extracts and samples containing cellular and particulate matter.

Still another object of the present disclosure is to provide a particle removal and droplet preparation device wherein the disclosed device can be easily integrated for qualitative and quantitative analysis with many different types of devices and instruments.

SUMMARY OF THE DISCLOSURE

In an embodiment, a method of particle removal and droplet preparation for qualitative and quantitative bio analysis includes filtering a sample fluid by passing through a lateral flow filter. The lateral flow filter is configured having at least one filter layer with a proximal end and a distal end, and the filtrate fluid is collected at the distal end of the filter layer. A droplet of filtrate fluid is ejected by applying pressure substantially at the distal end of the filter layer.

In one embodiment the disclosed device includes a lateral flow filter through which the sample is filtered such that the filtrate fluid is collected in the distal end of the filter matrix. The filtered fluid is made to eject from the matrix to form a droplet by pressing/squeezing the distal end of the filter only, with the help of a suitably shaped plunger means. In this embodiment it is possible to apply pressure at the distal end of the filter multiple times, without separating the distal end of the filter from the proximal end, which allows the residual plasma in the proximal end of the filter to be sucked repeatedly into the distal zone for maximum recovery of plasma.

In another embodiment the lateral flow filter is made up of several layers to form a filter module. The filter module is constructed to spread the sample drop quickly over a defined area and transports the filtered fluid to the distal end by another matrix. This design results in high efficiency of filtration in minimum time. The distal end is pressed/squeezed to allow ejection of the droplet of filtered fluid.

In another embodiment the pressing action of the plunger may be operated either manually or it may be accomplished by the insertion process of the device cassette in the Point of Care instrument or the Point of Care instrument can be programmed to press the plunger.

Still another embodiment of the invention allows for a buffer zone with low capillary force where the ejected filtrate droplet is allowed to be collected and then sucked into a reaction/receiving capillary zone with capillary force larger than the buffer zone but lower than the capillary forces of the distal end of filter matrix holding the filtered fluid. Such a configuration allows filtered fluid to flow into the reaction zone/receiving zone but it does not flow back into matrix when the pressing plunger is released.

In another aspect of the present disclosure, when the reaction zone/receiving zone is of well defined volume then it also acts as a device to collect predetermined volume of filtered fluid for analysis in the same device or in a different device.

DETAILED DESCRIPTION OF THE DISCLOSURE

Various embodiments of this invention describe novel devices for separating RBCs from a sample of blood and preparing a droplet of blood plasma for use with Point of Care instruments during assay procedures. However the applications of this disclosure are not limited to blood, and may be implemented in connection with separation of particulate matter from fluids such as fecaes, plant extracts and samples containing cellular and particulate matter, for preparing droplets for any kind of analysis including chemical and bio analyses, especially for use in the field and with Point of Care instruments.

Figure 1:
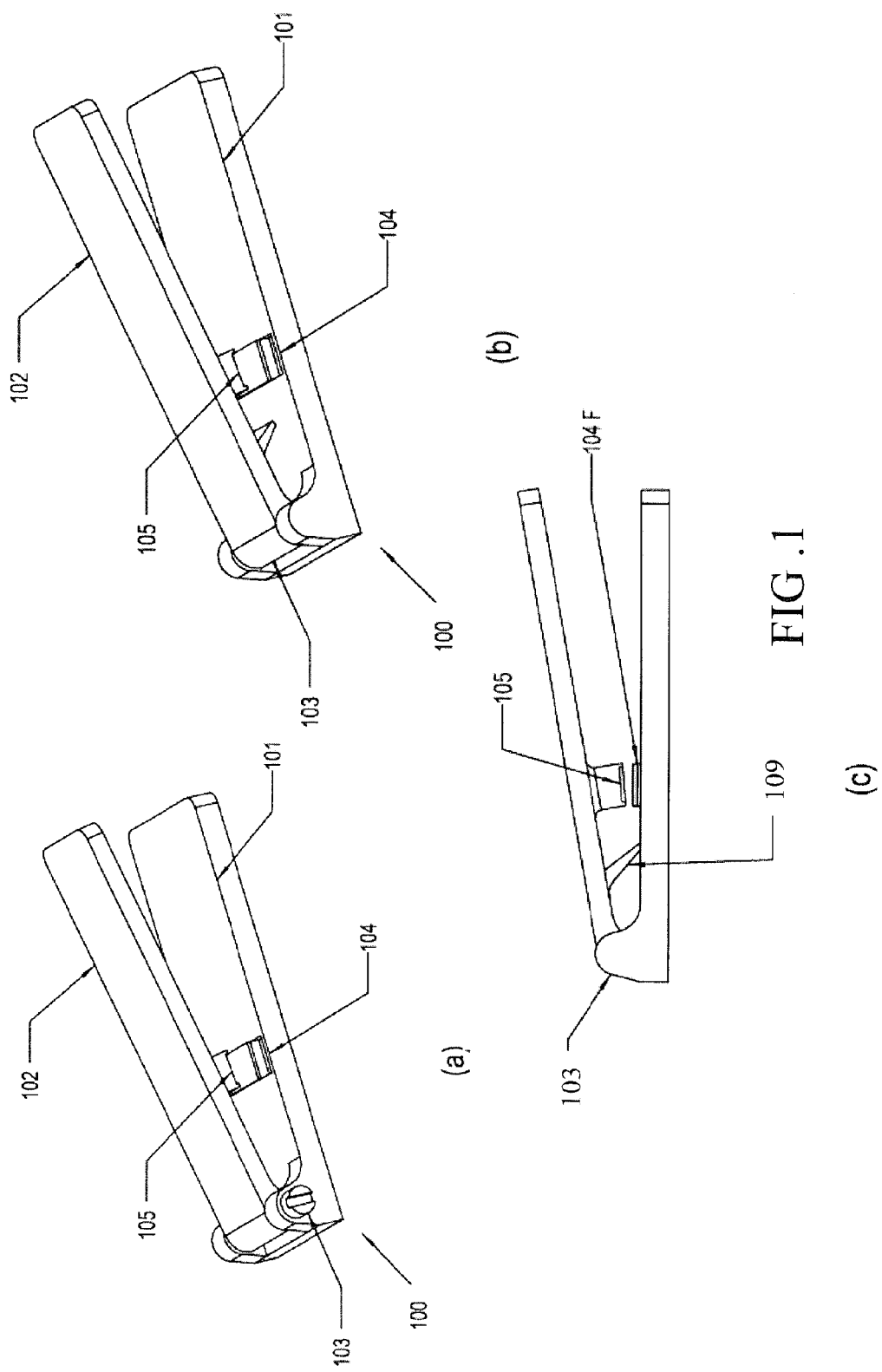
FIG. 1 (a-c) shows perspective views of a of a particle removal and droplet preparation device according to an embodiment of this disclosure.

FIG. 1 shows a perspective view of a particle removal and droplet preparation device (100) for qualitative and quantitative bioanalysis, according to an embodiment of this disclosure. Accordingly, the device (100) includes a base (101). A press rod (102) is pivotally connected to the base (101) through a hinge (103). A receptacle area (104) is provided at a substantially central location of the base (101). A plunger block (105) is provided in the press rod (102) at a location opposite to the receptacle area (104). A filter module (104F) is accommodated on the base (101) in the receptacle area (104) such that the distal end of the filter module (104) is directly beneath the plunger block (105) when the plunger rod (105) is pressed. The structure and functions of the filter module (104F) will be described in detail in the later part of this description.

In an example of the operation of the device (100) according to an embodiment of the disclosure, the base (101) may be configured stationary and the press rod (102) is movable towards the base (101) such that the plunger block (105) is positioned between pressing and non-pressing positions against the distal end of the filter module (104F).

In an example, the base (101) including the receptacle area (104), and the press rod (102) including the plunger block (105) is made from plastic material such as Polypropylene, ABS, Acrylics, Nylon, Polycarbonate or any other thermoplastic or thermosetting materials which fulfil the semi rigidity, flexibility, inertness, mouldability and cost requirements of the device. The base (101) including the receptacle (104) and the press rod (102) including the plunger block (105) can be rigidly shaped by a suitable manufacturing process that is known in the art. For example, the manufacturing process may be injection moulding. To persons skilled in the art it may be clear that the design of components can be made such that the number is minimized and assembly is very easy for example by a suitable snap fit design the hinge (102) is eliminated, and the spring action of the press rod (102) is obtained by a suitably designed flexible projection (109) (see FIG. 1C) in the press rod (102) or the base (101).

Figure 2:
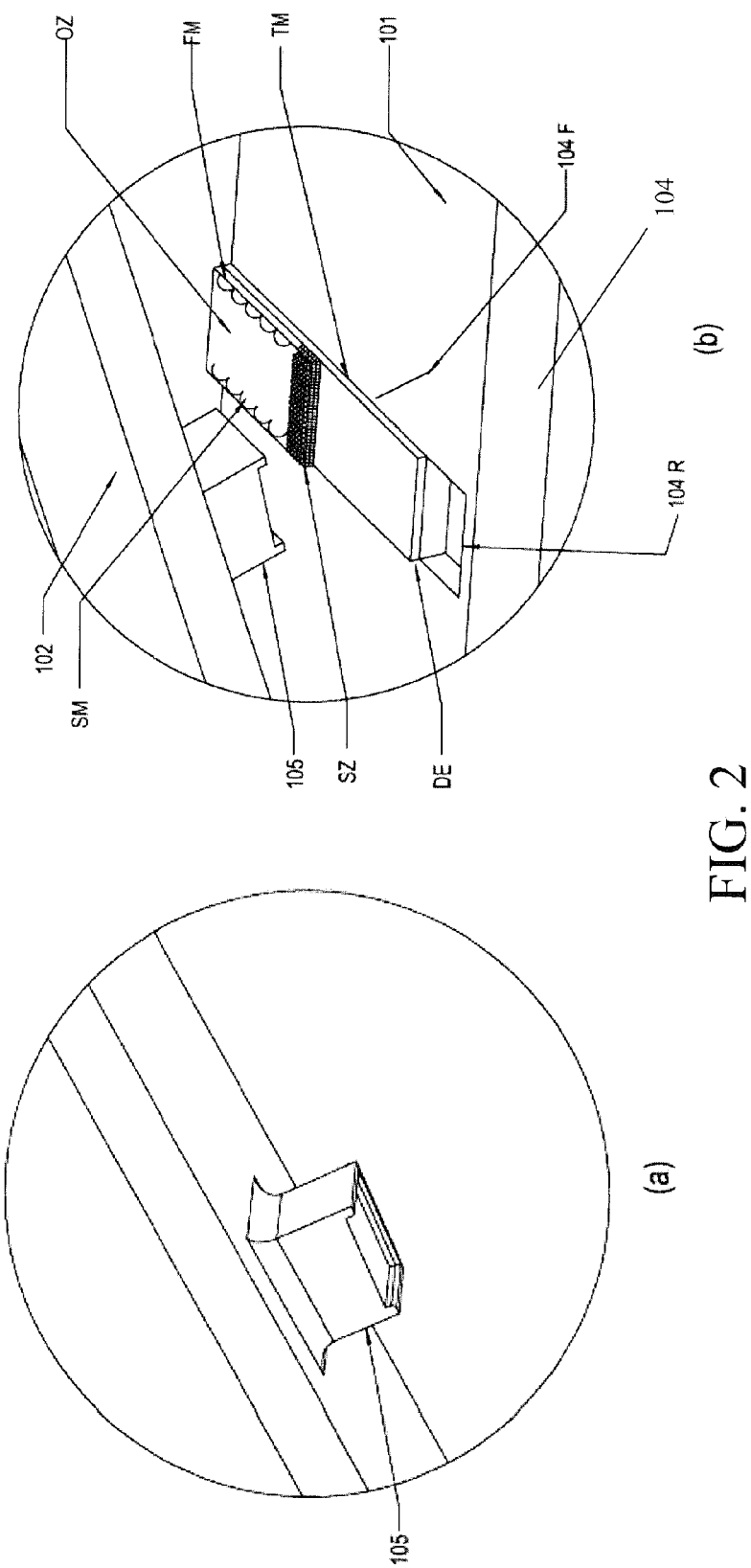
FIG. 2 (a-b) shows an exploded perspective view of the plunger block and the receptacle area having the filter module as part of a particle removal and droplet preparation device according to an embodiment of this disclosure.

FIG. 2 shows a perspective view of the plunger block (105) and the receptacle area (104) and its construction according to an embodiment of the disclosure. Accordingly, the receptacle area (104) accommodates the filter module (104F) and a reservoir (104R) provided adjoining the filter module (104F). The filter module (104F) is configured for filtering the particulate matter from the fluid sample and direct the filtered fluid sample towards the reservoir (104R) which is the distal end of filter module (104F). The reservoir (104R) is used to store a droplet of filtered fluid sample that can be used for quantitative or qualitative analysis in conjunction with a Point of Care device (not shown in the drawings).

Various embodiments of the filter module (104F) and systems for collecting and storing the droplet of filtered fluid for assay will be described in the further part of this description. FIG. 2a shows the exploded view of one example of construction of the plunger block (105) according to this disclosure. It should be noted that for the purposes of illustration, this disclosure refers to separation of RBCs from blood. This disclosure should not be construed to be limiting only to blood filtration and assay. The principles of this disclosure may also be implemented in connection with separation of particulate matter from samples of fluid such as fecaes, plant extracts and samples containing cellular and particulate matter, for preparing droplets for analytical and bioanalytical tests.

Figure 3:
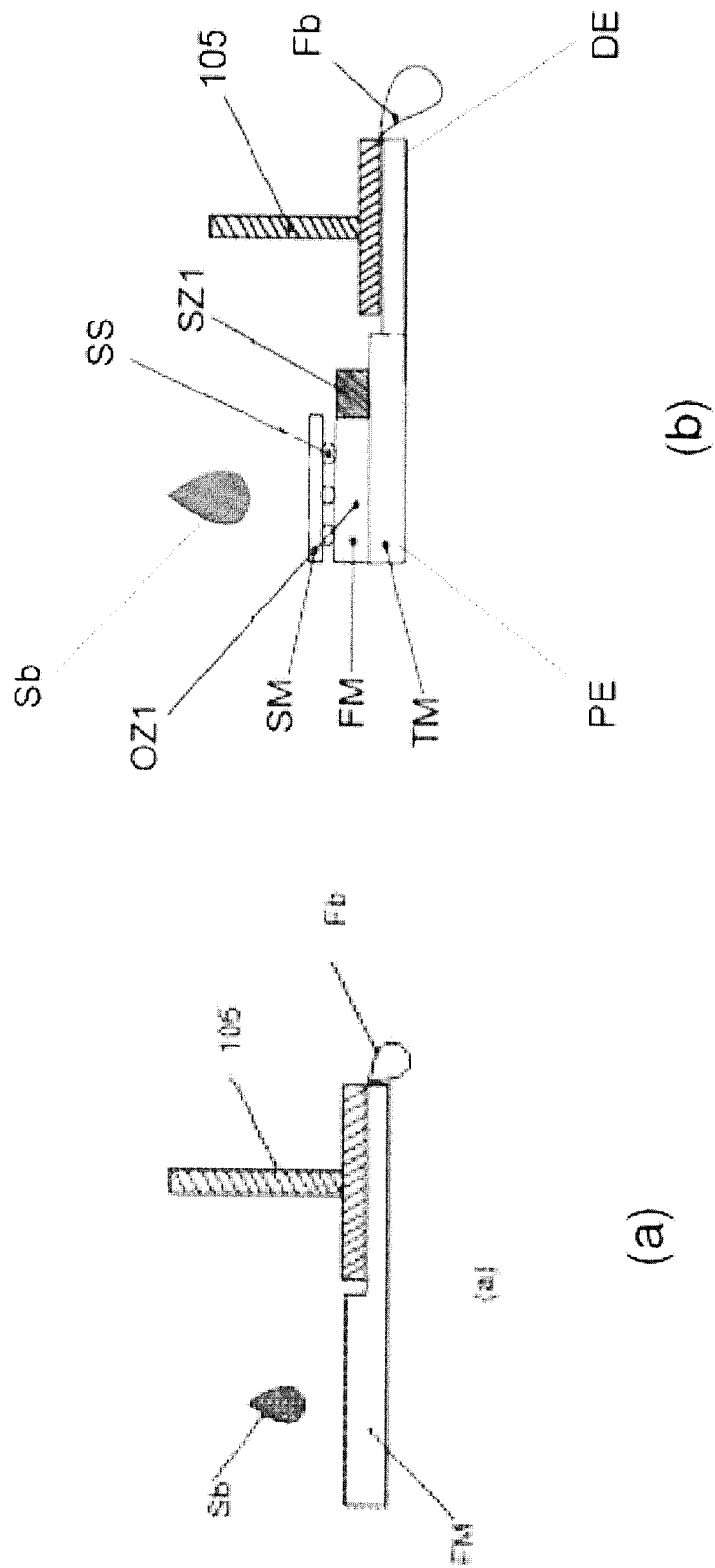
FIG. 3 (a-b) shows a schematic representation of filter module of a particle removal and droplet preparation device according to an embodiment of this disclosure

FIGS. 3a and 3b show a schematic representation of first embodiment of this disclosure. Accordingly, the filter module (104F) capable of retaining particles of interest module (104F) may be a single layer of lateral flow filter (see FIG. 3a) or it may be a multicomponent filter module (see FIG. 3b). The multicomponent filter Module includes a plurality of functional layers which enhance the performance of the device. The layers may include a sample matrix (SM), a filter matrix (FM) and a transport matrix (TM) stacked one over the other as shown as an example in FIG. 3b. An open zone (OZ1) and a sealing zone (SZ1) are provided in the filter matrix (FM). The transport matrix (TM) includes a proximal end (PE) and a distal end (DE). The plunger block (105) is configured to press the distal end (DE) of the transport matrix (TM) when a user operates the press rod (102) to move the plunger block (105) to press against the filter module (104F). An example of operation of the filter module (104F) will be described in the later part of this description.

In an example the material and construction of the sample matrix includes woven nets and nonwovens or paper made of plastic or natural filaments, yarns and fibers. The sample Matrix (SM) may be of open construction with pores of 10-100 microns and hydrophilic, to facilitate spreading the sample quickly over a predefined area.

In an example the material and construction of the filter matrix (FM) includes the materials well known in the art such as glassfiber, mixtures of glassfiber and cellulose fibers and plastic fibers or sintered materials, plain or impregnated with agglutinating agents. FM could also be polymeric membranes with desired retention capabilities. Typically pore size of FM may range from $0.1$-$10\mu$. The thickness may be selected based on retention efficiency of materials and volume of filtered fluid required.

The Transport Matrix (TM) may be made of hydrophilic materials with good capillary force and is of high void volume and high compressibility. Wet laid fibrous materials such as felts and glass papers are found useful for the application.

In an example the sealing zone (SZ1) is formed by filling the pores of the end of the Filter Matrix (FM) by a polymer which does not dissolve in the sample. Example of polymer include but are not limited to derivatives of cellulose such as Cellulose Acetate, Acrylates, Nylon, rubber cements etc. This effectively blocks the leakage of particulate matter from the edge of FM into Transport Matrix (TM).

In an example of operation of the filter module (104F), a drop of fluid sample (Sb) to be sampled is directed onto the sample matrix (SM). The sample matrix (SM) breaks the drop of sample (Sb) and instantly spreads the fluid sample (Sb) into the open zone (OZ1) of the filter matrix (FM). The sealing zone (SZ1) blocks the flow of fluid sample to transport matrix (TM) via a short path directly into the distal end (DE) of the transport matrix (TM). The filtered sample (Sb) filters through FM and also through transport matrix (TM) in a lateral flow mode and the filtered fluid is collected in the distal end (DE) of the Transport Matrix (TM). Thus, the arrangement of multiple and appropriate filter matrices (SM, FM, TM) as shown in FIG. 3b provides for efficient particulate (RBCs) retention. When the transport matrix (TM) is fully saturated, the distal end (DE) of transport matrix (TM) is embedded with (plasma) filtered fluid sample (Fb) due to strong capillary forces prevailing in the transport matrix (TM). When the user moves the press rod (102) to press against the filter module (104F), the plunger block (105) presses the distal end (DE) of the transport matrix (TM), which results in ejection of a droplet of filtered fluid sample (Fb) containing no additive or diluent. The filtered fluid sample (Fb) gets collected in the reservoir (104R). (refer FIG.

Figure 4:
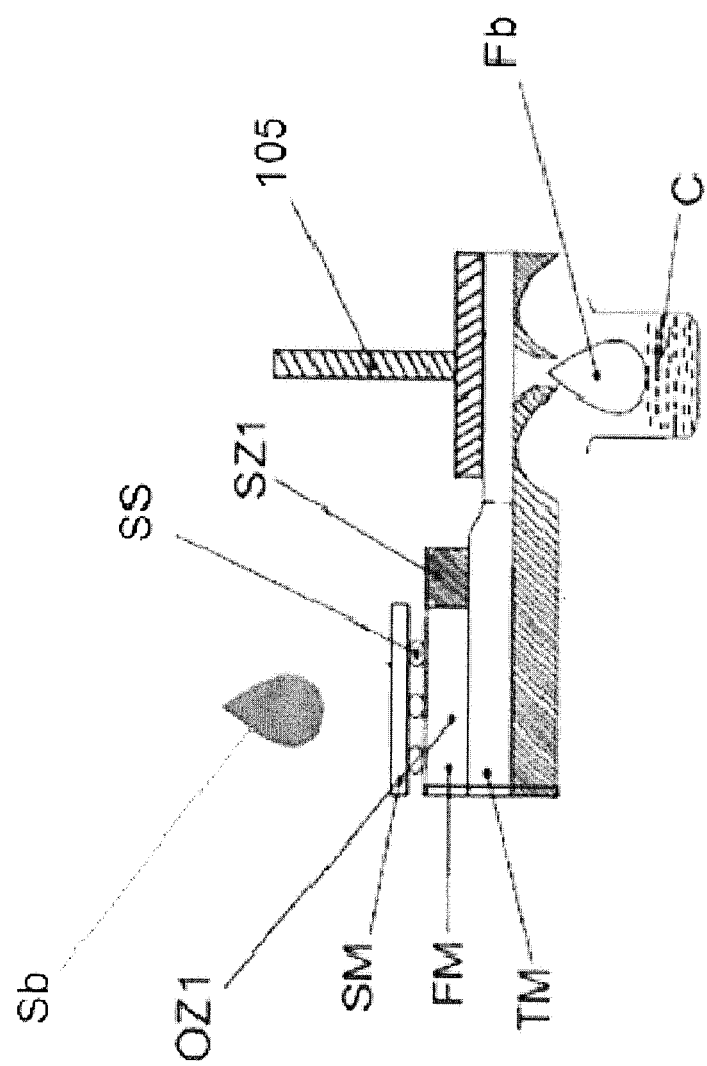
FIG. 4 shows a schematic representation of filter module of a particle removal and droplet preparation device using gravity flow for collecting droplet of filtered sample according to first embodiment of this disclosure.

2). Alternatively, the droplet of filtered sample (Fb) can also be collected in cuvette (C) for example, using gravity flow i.e. along a direction perpendicular to the filtration direction, as shown in FIG. 4. The volume of filtered fluid collected for analysis may vary from few microliters to several milliliters depending on the design of the device.

Figure 5:
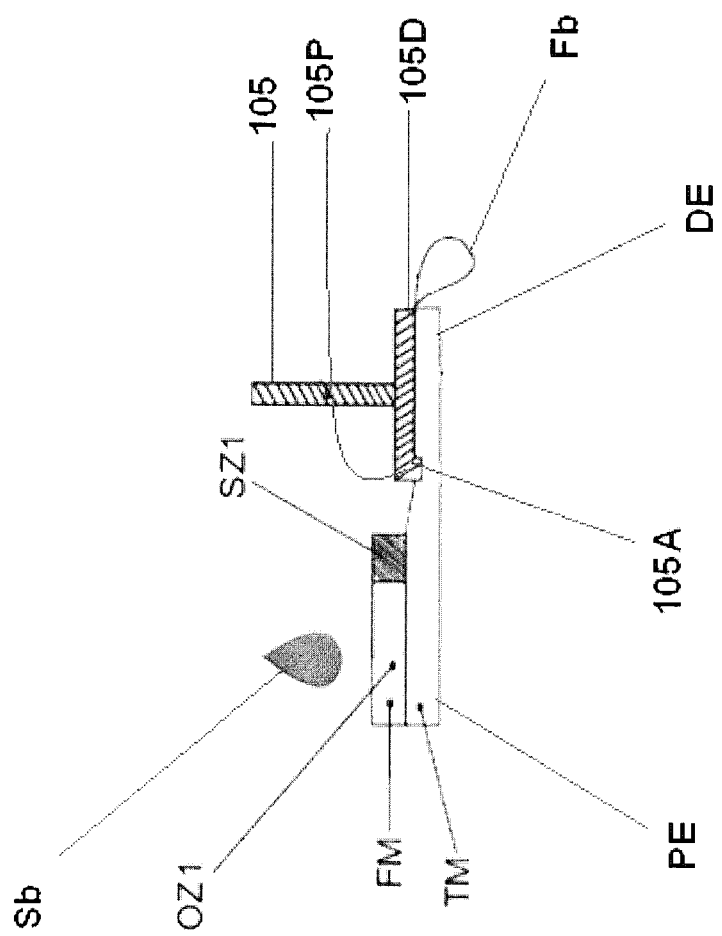
FIG. 5 shows a schematic representation of filter module and plunger block with projection according to second embodiment of this disclosure.

FIG. 5 shows a schematic representation of filter module (104F) according to second embodiment of this disclosure. In the example shown, the plunger block (105) includes a proximal end (105P) and a distal end (105D) wherein a projection (105A) is provided at the proximal end (105P) and/or on the edges of the plunger block (105) for making pinching contact with the transport matrix (TM) so as to minimize back flow and side flow of filtered fluid sample (Fb) into the filter matrix (FM). The droplet of filtered fluid sample (Fb) may be collected in the reservoir (104R). Alternatively, the filtered fluid sample (Fb) may be collected by gravity flow into a cuvette (not shown in FIG. 5).

Figure 6:
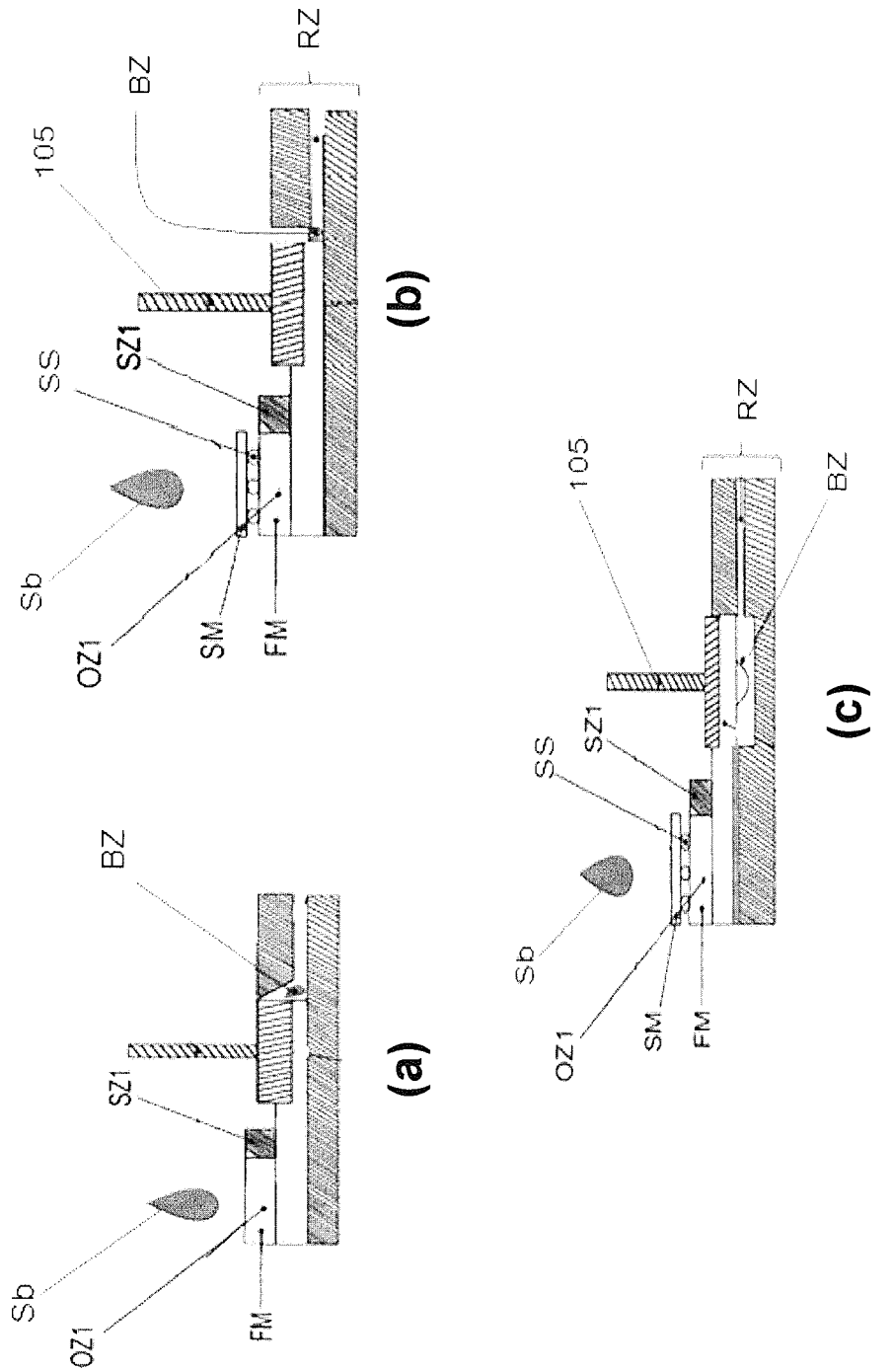
FIG. 6 (a-c) shows a schematic representation of filter module of a particle removal and droplet preparation device according to third embodiment of this disclosure, showing in a-c, examples of forms of buffer zones.

FIG. 6a-6c show a schematic representation of filter module (104F) according to third embodiment of this disclosure. Accordingly, the filter module (104F) includes a filter matrix (FM), a transport matrix (TM) and a capillary reaction and/or reading zone (RZ). The sample matrix (SM) may also be provided as shown in FIG. 6(b). A buffer zone (BZ) is provided in-between the distal end of the Transport Matrix (TM) and the capillary reaction and/or reading zone (RZ). The capillary force of the reaction and/or reading zone (RZ) is more than the capillary force of the buffer zone (BZ) but less than that of the Transport Matrix (TM). The capillary force of the buffer zone (BZ) is less than the capillary force of the Transport Matrix (TM).

The reaction and/or reading zone (RZ) may be a cuvette with capillary space of 0.025 to 0.5 mm which may contain reactants and also act as the zone for optical reading of the reaction products for quantitative analysis.

The reaction and/or reading Zone (RZ) may also be part of a microfluidic device which provide quantitative results of analytes in pure plasma (filtered fluid).

In an example, the plunger block (105) may be activated by the insertion process of the device in a Point of Care instrument or the Instrument may be programmed to press the plunger.

In an example of the operation of the filter module (104F) according to third embodiment of this disclosure, when the plunger block (105) is pressed, the filtered fluid sample (Fb) is transferred to the buffer zone (BZ) from the distal end (DE) of the transport matrix (TM). Since the capillary force of the buffer zone (BZ) is weaker than the capillary force of transport matrix (TM), the buffer zone (BZ) acts as a reservoir of droplet of the filtered fluid sample (Fb). The droplet of the filtered fluid sample (Fb) is sucked into the capillary reaction and/or reading zone (RZ) due to stronger capillary force of the capillary reaction and/or reading zone (RZ) as compared to the buffer zone (BZ). When the plunger is released, the filtered fluid sample (Fb) may be sucked back into the transport matrix (TM) since the capillary force of the buffer zone (BZ) is less than the capillary force of the Transport Matrix (TM). Simultaneously, suck back of the filtered fluid sample (Fb) from capillary reaction and/or reading zone (RZ) into the buffer zone (BZ) is avoided as the capillary force of the capillary reaction and/or reading zone (RZ) is more than the capillary force of the buffer zone (BZ).

FIG. 6b and FIG. 6c show second and third forms of buffer zone (BZ). In FIG. 6b, the buffer zone (BZ) is oriented along the direction of filtration. In FIG. 6b, the buffer zone (BZ) is oriented along a direction perpendicular to the filtration direction.

Thus, various embodiments of this disclosure provide device and method for removing particles from fluids and making droplets of fluids for qualitative and quantitative bioanalysis. Some embodiments of this disclosure provide a device for separating RBCs from blood and preparing a droplet of blood plasma for use with Point of Care instruments. Specific embodiments of this invention provide a filter module in combination with plunger to prepare a droplet of filtered sample for analysis.

Although the embodiments may be modified, all such modifications that may be obvious to a person skilled in the art will be deemed to be within the scope of the claims made herein.

The invention claimed is:

1. A device for enhancing recovery of a fluid sample during a qualitative and quantitative bioanalysis of said fluid sample, said device comprising,
a lateral flow filter module comprising a proximal end and a distal end;
a press rod operatively connected to a base;
a receptacle area positioned on the base for accommodating the filter module;
a plunger block provided on the press rod at a position substantially opposite to the receptacle area, wherein the distal end of the filter module is directly beneath the plunger block when the plunger block is pressed, and wherein the press rod is movable towards the base such that the plunger block is positioned between pressing and non pressing positions against the distal end of the filter module, wherein droplet of filtered fluid is ejected in the pressing position.

2. The device according to claim 1, wherein said press rod is connected to the base through a hinge.

3. The device according to claim 1, wherein a spring action is obtained between the base and the press rod.

4. The device according to claim 1, wherein the plunger block has a proximal end and a distal end, and wherein a projection is provided on the proximal end and/or on two edges of the plunger block.

5. The device according to claim 1, further comprising a buffer zone and a reaction and/or reading zone, wherein said filtered fluid is collected in said buffer zone and is subsequently passed to said reaction and/or reading zone through a capillary action.

6. The device according to claim 5, wherein capillary force of said buffer zone is less than that of said distal end of the filter module.

7. The device according to claim 5, wherein capillary force of said reaction and/or reading zone is less than that of distal end of the filter module and stronger than that of said buffer zone.

8. The device according to claim 1, wherein said fluid sample is blood and said filter system filters the Red Blood Cells components from said blood sample.

9. The device according to claim 8, wherein the device further comprising a sample spreader for spreading sample fluid over a predetermined area on the filter module.

10. The device according to claim 1, wherein the press rod is moved towards the base for squeezing and/or pressing manually.

11. The device according to claim 1, wherein the press rod is moved towards the base for squeezing and/or pressing by using a point of care instrument.

12. A particle and droplet preparation device for qualitative and quantitative bioanalysis comprising:
a lateral flow filter module comprising a proximal end and a distal end;

a press rod operatively connected to a base through a hinge;
a receptacle area positioned on the base for accommodating the filter module;
a plunger block provided on the press rod at a position substantially opposite to the receptacle area, wherein the distal end of the filter module is directly beneath the plunger block when the plunger block is pressed, and wherein the press rod is movable towards the base such that the plunger block is positioned between pressing and non pressing positions against the distal end of the filter module, wherein droplet of filtered fluid is ejected in the pressing position.

* * * * *